United States Patent [19]

Bouchard et al.

[11] Patent Number: 5,406,850
[45] Date of Patent: Apr. 18, 1995

[54] METHOD OF NON-DESTRUCTIVELY TESTING A SPUTTERING TARGET

[75] Inventors: Frederic Bouchard; Mark B. Dittmar, both of Grove City, Ohio

[73] Assignee: Tosoh SMD, Inc., Grove City, Ohio

[21] Appl. No.: 4,470

[22] Filed: Jan. 14, 1993

[51] Int. Cl.⁶ .............................. G01N 29/00
[52] U.S. Cl. ........................ 73/620; 73/616; 73/629; 204/298.03; 204/192.13
[58] Field of Search ............ 204/298.03, 192.13; 73/599, 610, 616, 620, 629

[56] References Cited

U.S. PATENT DOCUMENTS

| | | | |
|---|---|---|---|
| 3,914,987 | 10/1975 | Bickel et al. | 73/610 X |
| 4,334,433 | 6/1982 | Takahashi et al. | 73/629 |
| 4,539,848 | 9/1985 | Takafuji et al. | 73/599 |
| 4,624,127 | 11/1986 | Narushima et al. | 73/610 X |
| 4,719,583 | 1/1988 | Takafuji et al. | 364/506 |
| 5,038,615 | 8/1991 | Trulson et al. | 73/620 X |

OTHER PUBLICATIONS

"Scattering Induced Attenuation of Ultrasonic Backscattering", Peter Nagy et al., Dept. of Weld. Eng., Ohio State Univ., pp. 1263–1271.
"Nondestructive Determination of Grain Size . . . ," Hecht et al., Materials Evaluation/39/Sep. 1981, pp. 934–938.
"A New Measurement Method of the Grain Size . . . ," Takafuji et al., Nippon Steel Corp., Japan, pp. 195–200.
"Monitoring material grain size . . . ", Aharoni et al., Appl. Phys. Lett. 59(27) Dec. 30, 1991, pp. 3530–3532.
"Ultrasonic materials characterization," Smith, NDT International, vol. 20, No. 1, Feb. 1987, pp.43–48.
"Ultrasonic Grain Size Evluation of Heat-Treated Stainless Steel," Saniie et al., Dept. of E.& Comp. Eng., Ill. Inst. of Tech. et al.
"Frequency and Grain Size Dependency . . . ," Serabian, British Jour. of NDT, Mar. 1980, pp. 69–77.
Papadakis, E. P. "Methods of Experimental Phy., Ultrasonics," 19 ed. P.D. Edmonds; Academic Press, N.Y. (1981) pp. 237–298.
Smith, R. L., Reynolds, W. N., Wadley, H. N. G., "Met. Sci." 1981, 15, pp. 554–558.
Smith, R. L., Reynolds, W. N., "J. Mat. Sci.," 1982, 17, pp. 1420–1426.
Serabian, S., Williams, R. S., "Materials Evaluation," 1978, 24(3), pp. 55–62.
Hirone, T., Kamigaki, K., "Sci. Rpt. Tohoku Univ. First Series," 1955, A7, pp. 455–464.
Mason, W. P., "Physical Acoustics & the Properties of Solids", (Van Nostrand, N.Y., 1958).
Roth, W. J., "Appl. Phys.", 19, 1948, pp. 901–910.
Mason, W. P., et al., "Appl. Phys.", 19, 1948, pp. 940–946.

Primary Examiner—Herbert Goldstein
Assistant Examiner—Joseph L. Felber
Attorney, Agent, or Firm—Biebel & French

[57] ABSTRACT

A method of quality control for targets intended for use in the sputtering process. A test parameter is established by immersing the target in a tank of liquid, irradiating the target with ultrasonic energy in the Rayleigh frequency range, and integrating the portion of the ultrasonic energy which passes through the target and reflects off the back wall. This test parameter is closely related to the uniformity of a film which may be sputtered from the target onto a substrate.

8 Claims, 3 Drawing Sheets

METHOD OF NON-DESTRUCTIVELY TESTING A SPUTTERING TARGET

BACKGROUND OF THE INVENTION

This invention relates to quality control for sputtering targets. It relates more particularly to a method of non-destructively testing a sputtering target to obtain information indicative of the thickness uniformity of a layer of material which can be sputtered from the target onto a substrate. Even more particularly the invention relates to quality control of sputtering targets. Sputtering targets suitable for the practice of this invention frequently are of cylindrical configuration having a diameter of about 13 inches and an axial height of about 0.5 inches. Contemporary specifications for such targets call for an ability to sputter coat an 8 inch diameter substrate with a coating having a mean thickness of 1 micron and a standard deviation from that thickness of 0.01 micron or less. This means that at any point along the layer there must be a 63% probability that the thickness will deviate from 1 micron by less than the thickness of 50 atoms. In general, the sputtering process is able to meet such standards if the grain size of the target is sufficiently well controlled.

While it is possible to perform a microscopic examination of a sputtering target and to make qualitative judgements regarding the variation of grain size throughout the target, this is a very slow process. Moreover, the extreme quality requirements demand inspection of every target. Thus, optical inspection is not practical for controlling the quality of commercially produced sputtering targets.

It is well known that the grain size of a crystalline material affects the transmission of ultrasonic waves passing therethrough. Considerable work has been done in this regard in connection with grain size estimation of ferritic steels. Much of that work has involved experimental measurements in the Rayleigh scattering region; meaning that the grain size of the sample material is small compared to the wavelength of the ultrasonic energy. However, relatively little has been done to adapt that technology to the problem of mass production of high quality sputtering targets. Such work as has been done has not found any parameter which can be related to the thickness uniformity of a coating sputtered therefrom. Thus, there has been no effective method of controlling the quality of sputtering targets to assure the required performance.

SUMMARY OF THE INVENTION

It has been found in accordance with the practice of this invention that there is a strong correlation between integrated back wall reflection of ultrasonic energy in the Rayleigh wavelength region and uniformity of resulting film layer thickness. Preliminary data suggests that the best results are obtained when the crystallographic orientation of tested targets is approximately the same.

In accordance with the method of this invention, a sputtering target of a type having parallel front and back walls is submersed in a tank of liquid and is irradiated by a pulsed beam of ultrasonic energy having a wavelength approximately greater than or equal to ten times the nominal grain size.

A sonic receiving system receives the energy which is reflected from the target and integrates that portion thereof which is associated with back wall reflection. The integration is repeated for several pulses, and the average value is used as a product acceptance criterion. The measurement may be repeated for a series of two-dimensionally spaced points, and the resulting data may be digitally processed to obtain a mean integrated value and a standard deviation thereof.

The test results are compared with the results for a series of standard targets which have previously been measured and used in a sputtering process. Targets which deviate from a prescribed mean value for integrated back wall reflection amplitude are rejected.

DESCRIPTION OF THE PREFERRED EMBODIMENT

Figure 1:
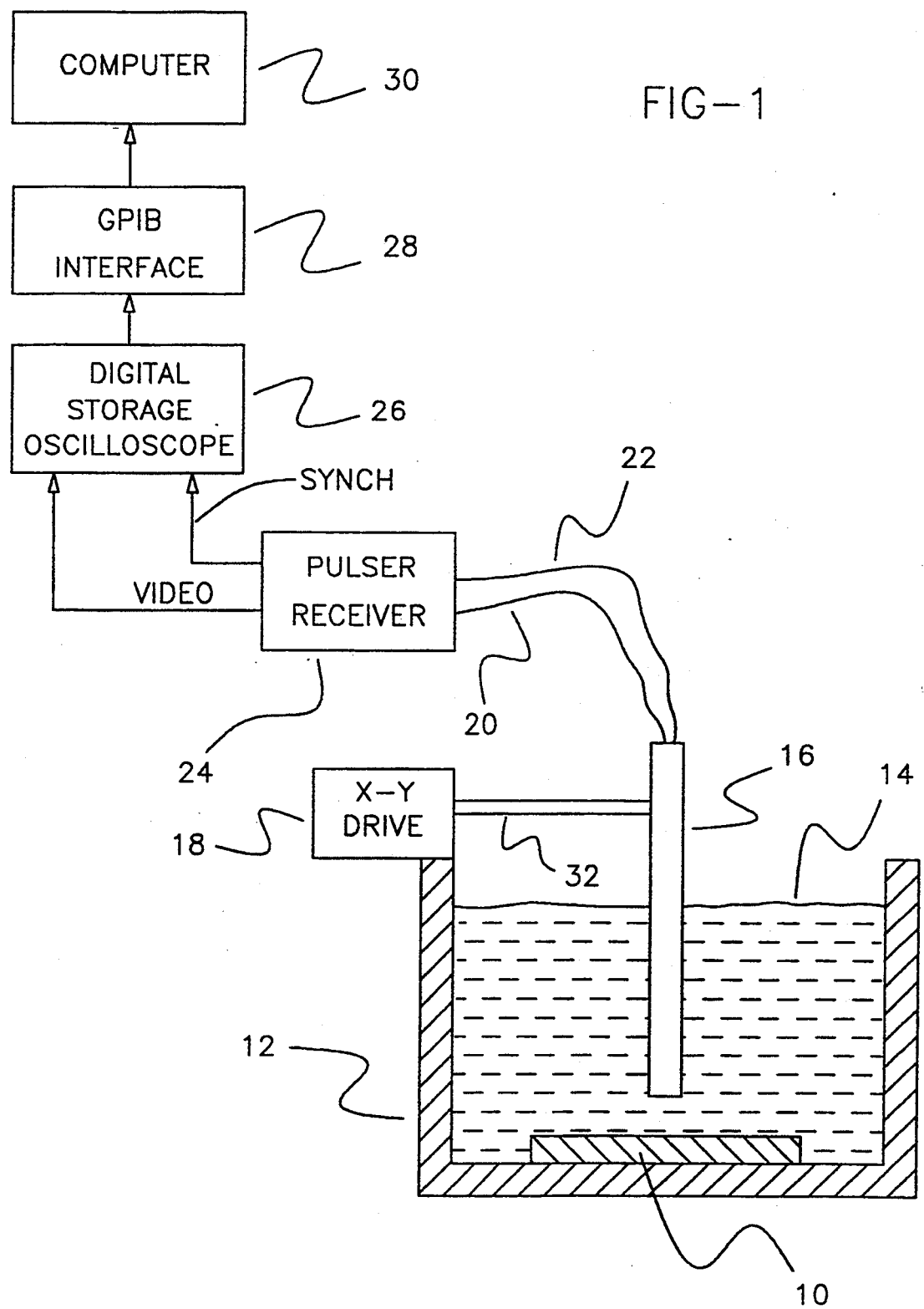
FIG. 1 is a schematic diagram of apparatus for nondestructively testing a sputtering target.
Figure 2:
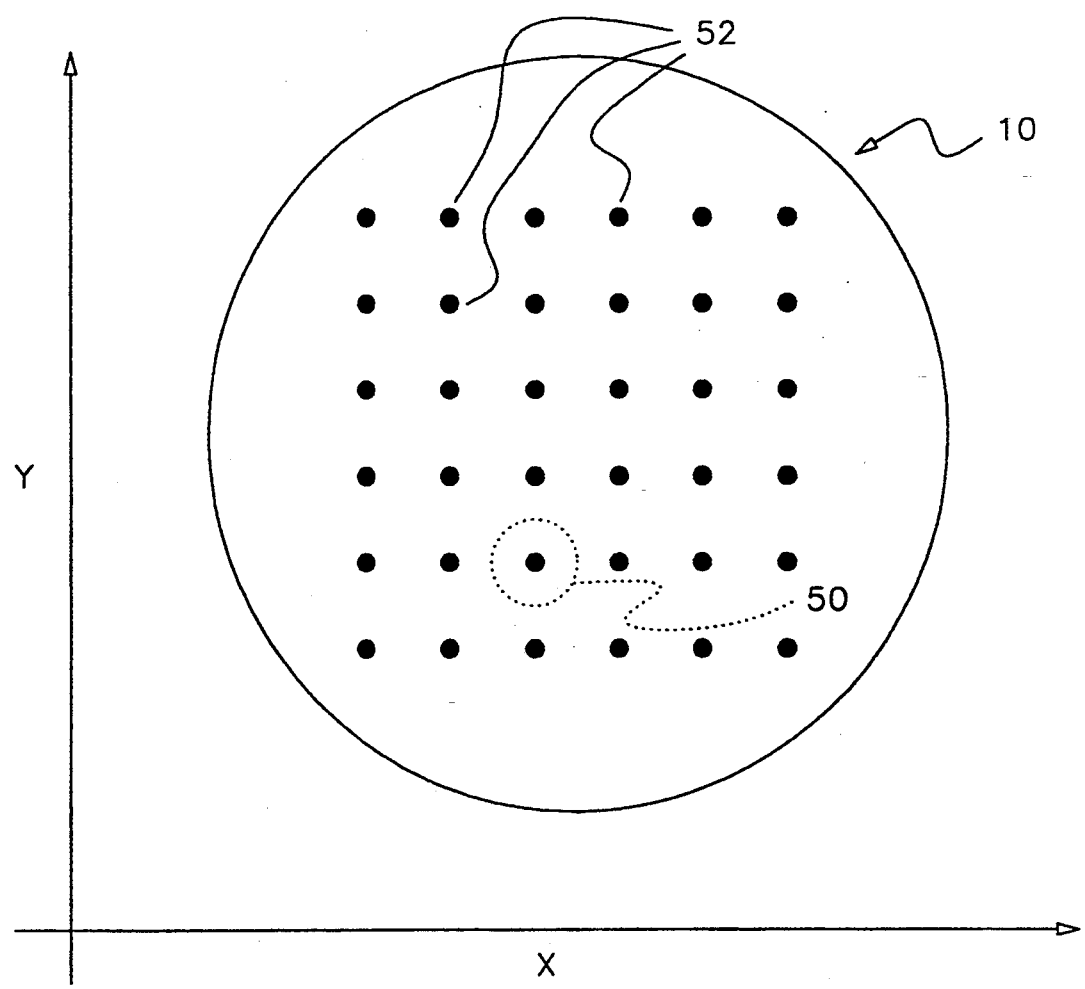
FIG. 2 is a schematic illustration of a pattern of test areas for a sputtering target.

Test equipment for practicing the method of this invention may be connected as illustrated generally in FIG. 1. Thus a sputtering target 10 may be placed in the bottom of a tank 12 and covered with deionized water or other suitable liquid 14. An ultrasonic transducer 16 is mounted on an arm 32 and suspended in the liquid 14 above the target 10. Target 10 may be of an aluminum based alloy, and transducer 16 may be of suitable size and configuration for transmitting and receiving ultrasonic energy at a frequency of about 0.5 MHz. Ultrasound at that frequency propagates through sputtering targets of interest with a wavelength of about 1.2 cm. The nominal grain size of the crystals comprising sputtering target 10 may be about 0.1 to 1 mm., and therefore the ultrasonic energy is in the Rayleigh frequency range. The height of the target 10 may be about 0.5 inches. Support arm 32 may be connected to an X-Y drive 18, so that transducer 16 may be scanned across the surface of target 10. In one embodiment of the invention transducer 16 may view an area 50 as illustrated in FIG. 2 centered at a scan position 52. Transducer 16 may be moved successively to a series of 36 scanning positions arranged in a 6×6 matrix. At each position transducer 16 may irradiate target 10 with a series of ultrasonic pulses; about 10 pulses being typical. Echoes which are backwardly reflected by target 10 are received by transducer 16.

Transducer 16 is connected to a pulser/receiver 24 by a pair of lead lines 20,22. Pulser/receiver 24 sends a series of driving pulses to transducer 16 and receives a return signal for each transmitted pulse. Pulser/receiver 24 processes the received signals and supplies a synchronizing signal and a video signal to a digital storage oscilloscope 26. The digital storage oscilloscope has an integrating gate which is manually positioned on a selected coherent back wall reflection peak. The amplitude of the signal is integrated over the time period of the gate, and oscilloscope 26 effectively measures the area under the portion of the signal trace which falls within the gate.

Figure 3:
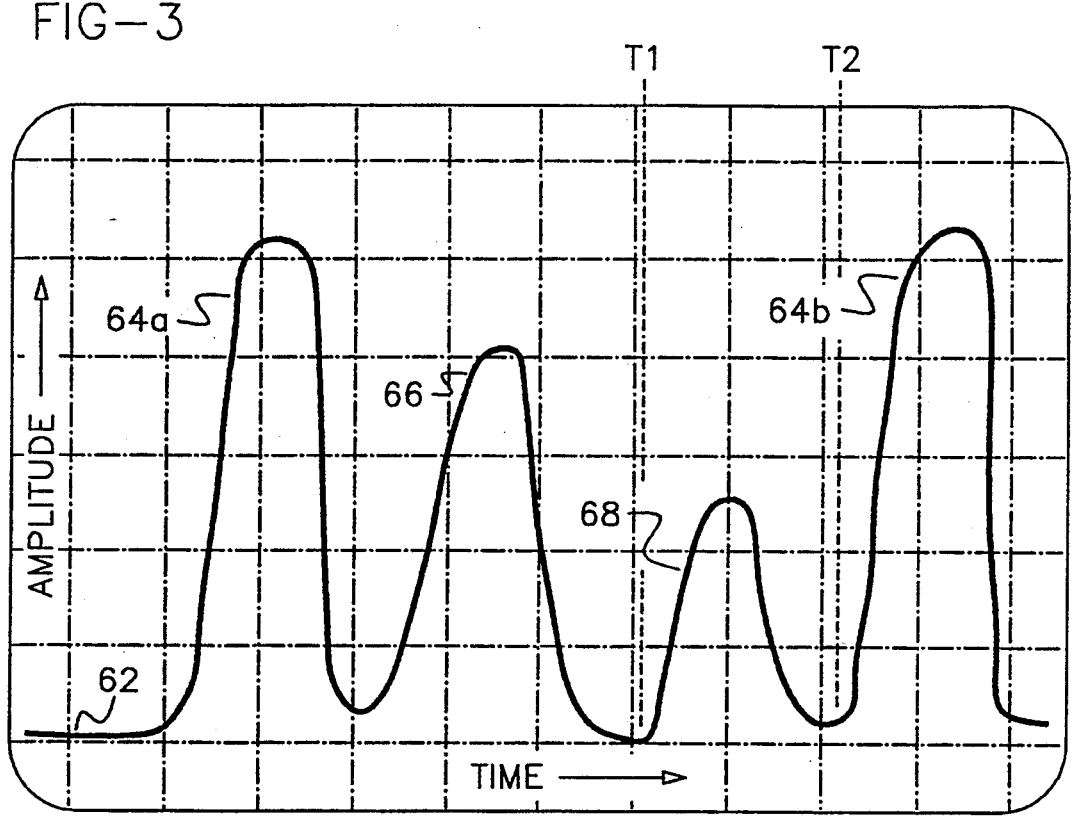
FIG. 3 is an illustration of a typical oscilloscope presentation of ultrasonic energy reflected by a sputtering target and received by a receiver.

Referring now to FIG. 3, reference numeral 60 indicates a typical video presentation appearing on the viewing screen of oscilloscope 26 during the practice of this invention. Signal trace 62 indicates the instantaneous voltage developed at pulser/receiver 24 as a consequence of sonic echoes received by transducer 16. That voltage is characterized by a pair of peaks 64a and 64b which represent front face reflections associated with a pair of successively transmitted ultrasonic pulses. A pair of peaks 66,68 are coherent reflection signals from the back wall of target 10. The integrating gate of digital storage oscilloscope 26 may be set to straddle either one of peaks 66 or 68. As illustrated in FIG. 3, the integrating gate of digital storage oscilloscope 26 is set on peak 68 so as to integrate the amplitude of trace 62 during the time period from T1 to T2. This integrated amplitude is digitized and transmitted to computer 30 via GPIB interface 28.

GPIB is an acronym for General Purpose Interface Bus. This interface is defined by ANSI/IEEE Standard 488.1-1987 and is also known as the IEEE 188 interface bus. Thus GPIB interface 28 is a well-known and widely used apparatus which is able to pass hardware specific data from digital storage oscilloscope 28 to computer 30.

Computer 30 averages the integrated reflected amplitude for a fixed number of back wall reflections and then instructs X-Y drive 18 to position transducer 16 at a new position. The average values for each of the positions, such as positions 52 of FIG. 2 are stored by computer 30 and then averaged to compute a mean integrated back wall reflection signal for the target 10 as a whole. For quality control purposes a standard deviation may also be calculated. Targets which do not meet established standards for both the mean and the standard deviation may be rejected. Alternatively, a target may be rejected if the average integrated reflection at any location is outside a specified range. It will be understood that acceptance standards will vary with target composition and specific target geometry. Standards are established by testing "standard" targets and then using them to sputter coat "standard" substrates.

Figure 4:
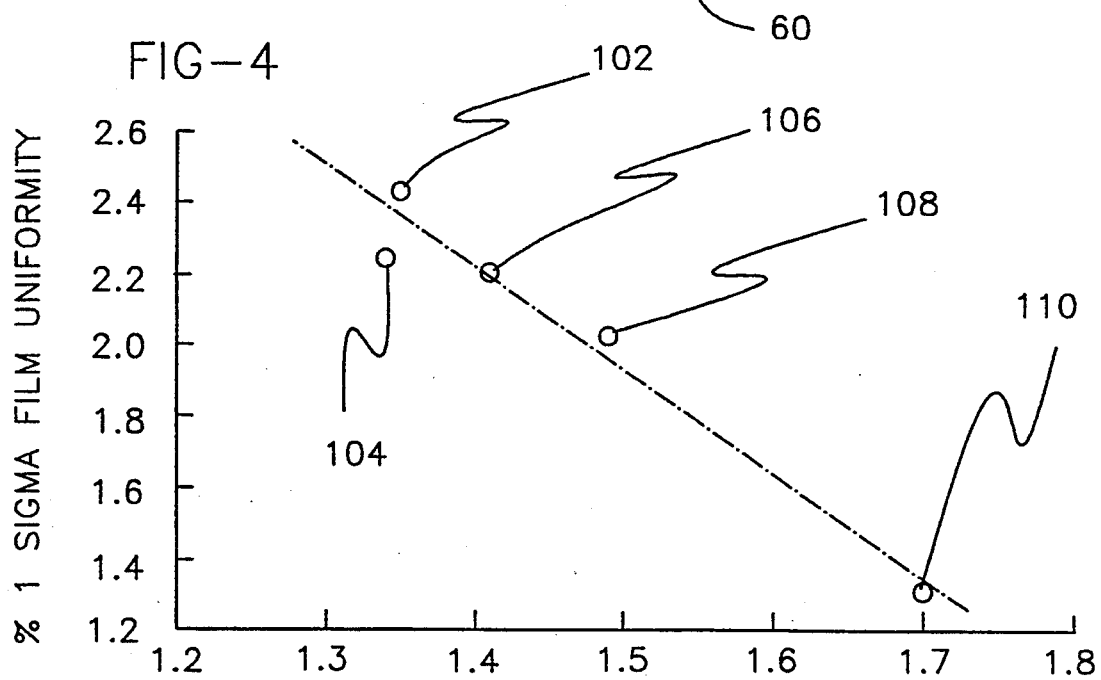
FIG. 4 is a plot showing the relationship between a mean value of integrated amplitude of back wall reflection and sputter coating performance.

If a series of standard targets are tested and then sputter coated on an appropriate wafer, the film thickness has been found to vary with integrated back wall reflection amplitude in the manner illustrated in FIG. 4. The graph of FIG. 4 was compiled from test data for a set of 5 Al 0.5 Cu planar targets of 13 in. diameter and 0.5 in. height. These targets were sputter coated on 8 inch wafers. The integrated reflected amplitude was measured and averaged for 10 pulses at each of 225 positions on each target. Data points for the tested targets are numbered 102, 104, 106, 108, and 110, respectively. The data shows a strong correlation between integrated back wall reflection amplitude and standard deviation of coating thickness variation.

The crystallographic orientation of the tested targets was measured by X-ray diffraction and was determined to be as follows:

| Tested Target | | |
| --- | --- | --- |
| 102 | $<100> = 22.3$; | $<110> = 18.00$ |
| 104 | $<100> = 27.2$; | $<110> = 13.4$ |
| 106 | $<100> = 21.2$; | $<110> = 14.0$ |
| 108 | $<100> = 28.8$; | $<110> = 14.0$ |
| 110 | $<100> = 23.3$; | $<110> = 16.8$ |

While the method herein described constitutes a preferred embodiment of this invention, it is to be understood that the invention is not limited to this precise method, and that changes may be made without departing from the scope of the invention, which is defined in the appended claims.

What is claimed is:

1. A method of non-destructively testing a sputtering target having parallel front and back walls and comprising sputtering material of an approximately known nominal grain diameter, wherein a test parameter is obtained that is predictably related to the standard deviation of variations from a mean thickness for a thin film of material to be sputtered from said target to a substrate, said method comprising the steps of:

(1) submersing said target in a tank of liquid,
    (2) directing a pulsed beam of sonic energy from a transmission point through said liquid and toward said target, said sonic energy having a frequency such that its wavelength in said target is substantially greater than said nominal grain diameter and said beam being directed such that a portion thereof passes through said front wall, reflects off said back wall, passes again through said front wall and travels to a reception point having a predetermined position relative to said transmission point,
    (3) sensing said beam portion at said reception point and generating a corresponding sensing signal, and
    (4) integrating said sensing signal with respect to a specified time period to create said test parameter.

2. The method according to claim 1, further comprising the steps of:

(5) sequentially directing said pulsed beam of sonic energy toward a plurality of separate locations on said target,
    (6) repeating said steps (2) through (4) for each of said locations to create a plurality of values for said test parameter, and
    (7) calculating the mean value of said plurality of values.

3. A method of non-destructively testing a sputtering target having paralell front and back walls comprising sputtering material of an approximately known nominal grain diameter, wherein a test parameter is obtained that is predictably related to the standard deviation of variations from a mean thickness for a thin film of material to be sputtered from said target to a substrate, said method comprising the steps of:

(1) submersing said target in a tank of liquid,
    (2) directing a series of pulses of sonic energy from a transmission point through said liquid and toward a predetermined location on said target, said sonic energy having a frequency such that its wavelength in said target is substantially greater than said nominal grain diameter and said pulses being directed such that at least portions thereof pass through said target, reflect off said back wall, and travel to a reception point having a predetermined position relative to said transmission point,
    (3) sensing said pulse portions and generating corresponding sensing signals,
    (4) integrating each of said sensing signals with respect to a specified time period to create integrated values thereof, and
    (5) averaging said integrated values to obtain said test parameter.

4. The method according to claim 3, wherein said steps (2) through (5) are repeated for a plurality of separate locations on said target to obtain a plurality of values for said test parameter, said test parameter values being used to establish a pass/fail result for said target.

5. The method according to claim 4, further comprising the step of calculating the mean value of said plurality of test parameter values.

6. The method according to claim 5, further comprising the step of calculating the standard deviation of said plurality of test parameter values.

7. The method according to claim 3, further comprising the steps of:

(6) sputtering a film from said target onto a substrate, (7) measuring the thickness of said film at a plurality of locations on said substrate, (8) calculating a standard deviation of said film thickness, (9) using said test parameter and the standard deviation of said film thickness to establish a standard value for said test parameter,

(10) non-destructively testing a plurality of additional sputtering targets according to steps (2) through (5), and

(11) comparing said standard value with values of said test parameter measured for said additional targets.

8. The method according to claim 3, wherein said transmission point and said reception point are coincident and a common transducer is used for directing sonic energy toward said target and sensing reflections therefrom.

* * * * *